(12) United States Patent
Yu et al.

(10) Patent No.: US 8,282,948 B2
(45) Date of Patent: Oct. 9, 2012

(54) CAMOMILE TREATED GLOVE (75) Inventors: Loo Liong Yu, Subang Jaya/Selangor (MY); Hee Meng Lai, Melaka (MY); Noorzanita Binti Muhammad Zain, Kelantan (MY); Adeli Kassim, Melaka (MY)

(73) Assignee: Ansell Healthcare Products, Inc., Red Bank, NJ (US)

( * ) Notice: Subject to any disclaimer, the term of this patent is extended or adjusted under 35 U.S.C. 154(b) by 219 days.

(21) Appl. No.: 12/642,824

(22) Filed: Dec. 20, 2009

(65) Prior Publication Data

US 2010/0150977 A1    Jun. 17, 2010

Related U.S. Application Data (63) Continuation of application No. 10/321,897, filed on Dec. 17, 2002, now abandoned.

(51) Int. Cl.
*A61K 8/00* (2006.01)

(52) U.S. Cl. ....................................................... 424/401

(58) Field of Classification Search ........................ None
See application file for complete search history.

(56) References Cited

U.S. PATENT DOCUMENTS

| | | |
|---|---|---|
| 4,122,554 A | 10/1978 | Stager |
| 4,185,330 A | 1/1980 | Stager |
| 4,186,445 A | 2/1980 | Stager |
| 4,585,650 A | 4/1986 | Newberry et al. |
| 4,775,372 A | 10/1988 | Wilberg |
| 4,809,365 A | 3/1989 | Chen et al. |
| 4,820,508 A | 4/1989 | Wortzman |
| 5,003,638 A | 4/1991 | Miyake et al. |
| 5,019,096 A | 5/1991 | Fox et al. |
| 5,075,340 A | 12/1991 | Barua et al. |
| 5,208,013 A | 5/1993 | Klein |
| 5,417,968 A | 5/1995 | Staats |
| 5,500,957 A | 3/1996 | Stein |
| 5,614,202 A | 3/1997 | DeFina |
| 5,682,617 A | 11/1997 | Tumas |
| 5,716,625 A | 2/1998 | Hahn et al. |
| 5,869,072 A | 2/1999 | Berry |
| 5,910,567 A | 6/1999 | Tanaka et al. |
| 5,945,409 A | 8/1999 | Crandall |
| 6,117,119 A | 9/2000 | Gould |

(Continued)

FOREIGN PATENT DOCUMENTS

JP    58-042281    10/1982

(Continued)

OTHER PUBLICATIONS

Held, Elizabeth et al., "The Combined use of Moisturizers and Occlusive Gloves: An Experimental Study", *American Journal of Contact Dermatitis*, vol. 10, No. 3; Denmark, (Sep. 1999),146-152.

(Continued)

*Primary Examiner* — Robert A Wax
*Assistant Examiner* — Melissa Mercier
(74) *Attorney, Agent, or Firm* — Moser Taboada (57) ABSTRACT

The present invention is directed to a glove wherein the interior surfaces of the glove contain a film which includes water, glycerol and a botanical extract.
Further embodiments of the invention are directed to the composition of the film and the process for applying the film onto the interior surfaces of the glove.

26 Claims, 4 Drawing Sheets

Tumbling Of Wet Gloves

U.S. PATENT DOCUMENTS

| | | | |
|---|---|---|---|
| 6,153,208 | A | 11/2000 | McAtee et al. |
| 6,153,209 | A | 11/2000 | Vega et al. |
| 6,168,798 | B1 * | 1/2001 | O'Halloran et al. .......... 424/401 |
| 6,221,346 | B1 | 4/2001 | Streels |
| 6,274,154 | B1 * | 8/2001 | Chou ........................... 424/402 |
| 6,294,186 | B1 | 9/2001 | Beerse et al. |
| 6,395,701 | B1 | 5/2002 | Connor et al. |
| 6,423,328 | B2 | 7/2002 | Chou et al. |
| 6,630,152 | B2 | 10/2003 | Chou |
| 6,692,756 | B2 | 2/2004 | Chou et al. |
| 2002/0025335 | A1 | 2/2002 | Chou |
| 2002/0110584 | A1 | 8/2002 | Chou |
| 2003/0017193 | A1 | 1/2003 | Chou |
| 2004/0115250 | A1 | 6/2004 | Loo et al. |
| 2004/0122382 | A1 | 6/2004 | Johnson et al. |
| 2006/0140924 | A1 | 6/2006 | Schroeder et al. |

FOREIGN PATENT DOCUMENTS

| | | |
|---|---|---|
| JP | 9002962 | 1/1999 |
| JP | 11-229211 | 8/1999 |
| JP | 11229211 | 8/1999 |
| JP | 2002-523193 | 7/2002 |
| JP | 2003-64514 | 3/2003 |
| JP | 2003-510132 | 3/2003 |
| WO | WO-94/12115 | 6/1994 |
| WO | WO-00/59450 | 10/2000 |
| WO | WO-00/65911 | 11/2000 |

OTHER PUBLICATIONS

Metules, Terri J., "Tips for Nurses Who Wash Too Much", *RN Magazine*; vol. 63, No. 3; Montvale, New Jersey, (Mar. 2000),34-37.

Maines De Soie Skin Care Gloves, *Lookout-Nonfoods*, p. 057NF, vol. XIX, issue 6, (Mar. 26, 1996).

ISR From PCT/US03/38853, 1, Sep. 20, 2004.

EP Search Report, 2, Jul. 2, 2007.

IPER From PCT/US03/38853, 3, Sep. 20, 2004.

US 6,680,064, 01/2004, Chou (withdrawn)

* cited by examiner

FIG. 1 Tumbling Of Wet Gloves

FIG. 2 Spraying Of Moisturizers Mixture into Tumble Dryer

FIG. 3 Continue Spraying And Tumbling

FIG. 4 Drying Process

CAMOMILE TREATED GLOVE

CROSS-REFERENCE TO RELATED APPLICATION

This application claims the benefit of priority to U.S. patent application Ser. No. 10/321,897, filed Dec. 17, 2002, which is hereby incorporated by reference in its entirety.

TECHNICAL FIELD

This invention relates to a disposable glove treated with a composition containing water, glycerol and a botanical extract and the process for applying the composition onto the interior surfaces of the glove.

BACKGROUND

Disposable gloves are widely used as a protective measure to insulate hands from microorganisms and irritants. Many workers, especially those working in the health care, chemical and food handling industries, rely on disposable gloves to provide a protective barrier from harmful microorganisms and irritants. Additionally, the increasing threat of exposure to bio-terrorism has prompted many individuals to wear disposable gloves to protect themselves against deadly microorganisms. Consequently, more individuals are wearing disposable gloves for much longer periods of time than in the past.

Disposable gloves are typically made from latex and vinyl materials which tend to dry and irritate human skin. With the increased use of disposable gloves comes a need to provide a disposable glove that is comfortable to wear and will not dry and irritate the hands of the wearer.

Many botanical extracts have been found to soften and soothe dry and irritated skin. Aloe vera is a well known extract from the aloe plant. Aloe vera is commonly used to treat burns because of its healing, cooling, and moisturizing effects. Camomile is also a well known herb commonly used in teas, but has been found to exhibit anti-inflammatory properties when applied topically.

U.S. Pat. No. 6,274,154 is directed to a disposable glove containing a film of dehydrated aloe vera on the interior surface of the glove. This patent describes applying a solution of aloe vera to the interior surface of a glove, then heating the glove until the water is dehydrated, leaving a film of dehydrated aloe vera on the interior surface of the glove. Since the water is completely dehydrated, the interior surfaces of the glove do not contain any significant amount of moisture. Since no moisture is present, the dehydrated aloe vera peels off as powder thereby minimizing any moisturizing effect.

The present invention fills a present need of providing a glove that is non-irritating to the skin and moisturizes the skin as it is worn.

BRIEF SUMMARY

The present invention is directed to a glove wherein the interior surfaces of the glove contain a film which includes water, glycerol and a botanical extract, the water present in an amount ranging from about 30 mg to about 90 mg per glove.

Another embodiment of the invention is directed to a method of applying a film to the interior surfaces of a glove which includes washing a cured glove, drying the washed glove in a tumbler dryer at a temperature of about 50 to about 55° C., spraying a solution into the tumbler dryer while the washed glove is drying and is partially wet, and drying the washed glove until a film forms on the interior surfaces of the washed glove.

A further embodiment of the invention is directed to a composition containing water, glycerol, camomile, a thickener, an anti-blocking wax, a wetting agent, a fragrance, a silicone emulsion and a preservative.

DETAILED DESCRIPTION

Figure 1:
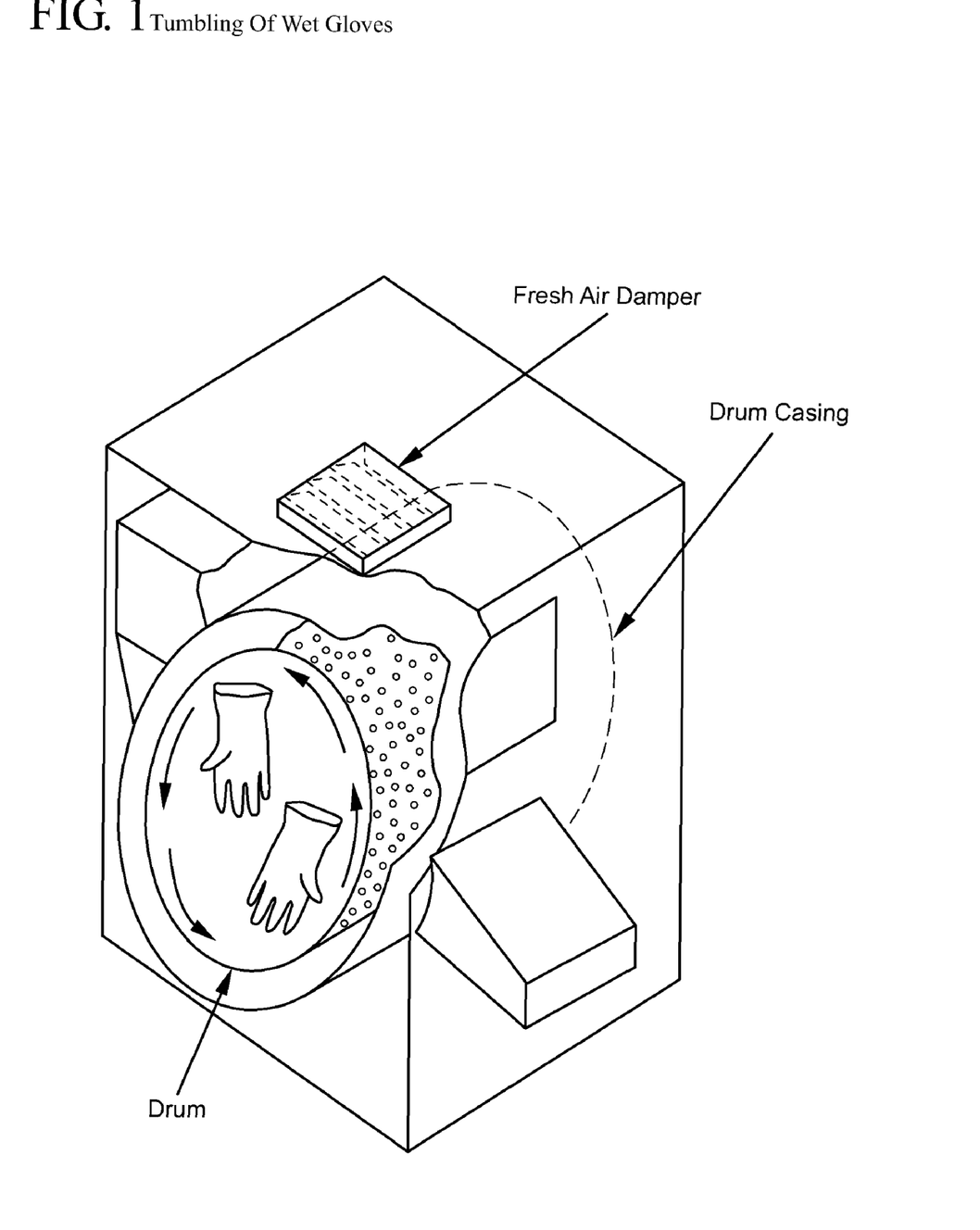
FIG. 1 illustrates wet gloves drying in a tumble dryer after being washed.
Figure 2:
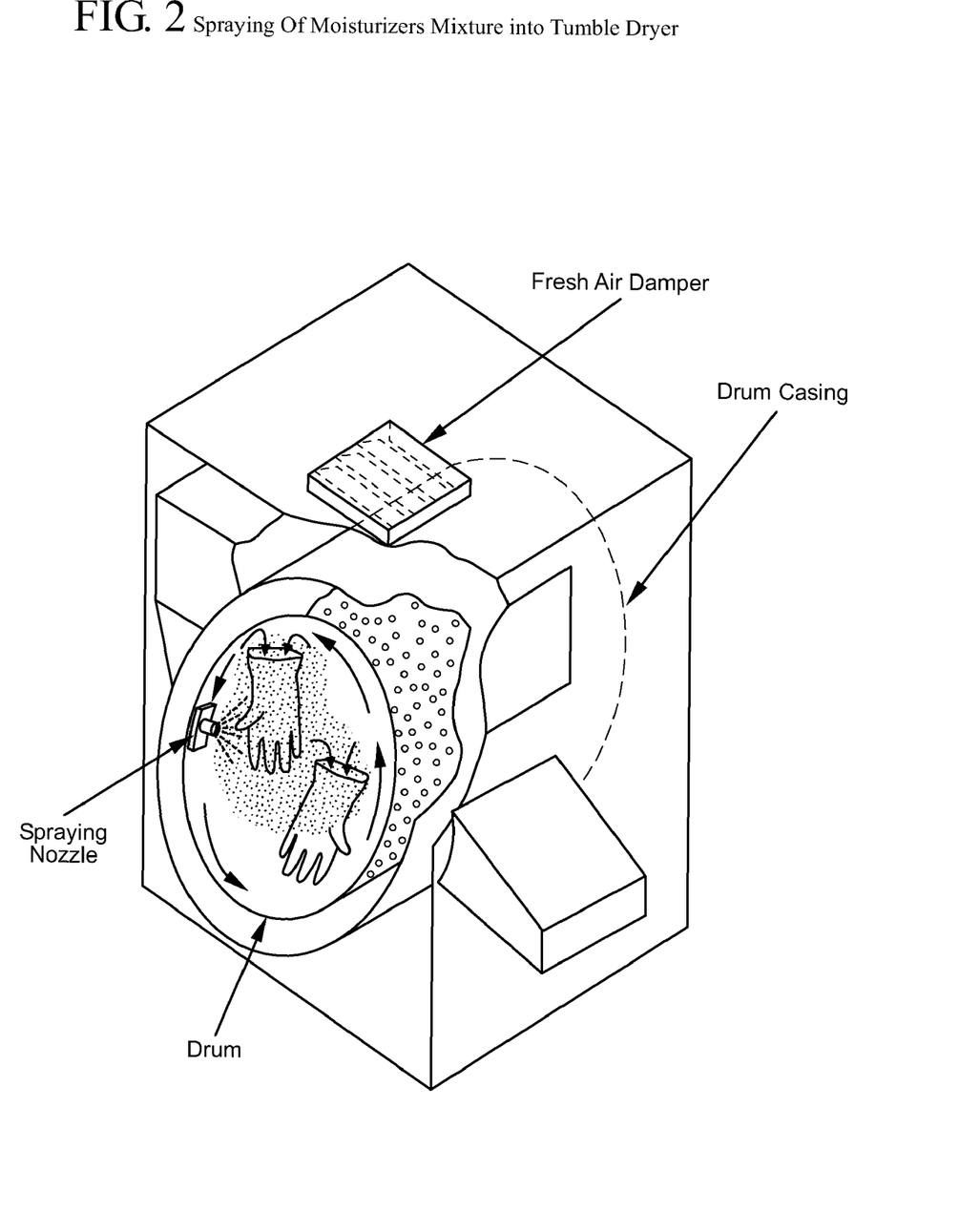
FIG. 2 shows spraying the moisturizing mixture into the tumble dryer while the gloves are drying.
Figure 3:
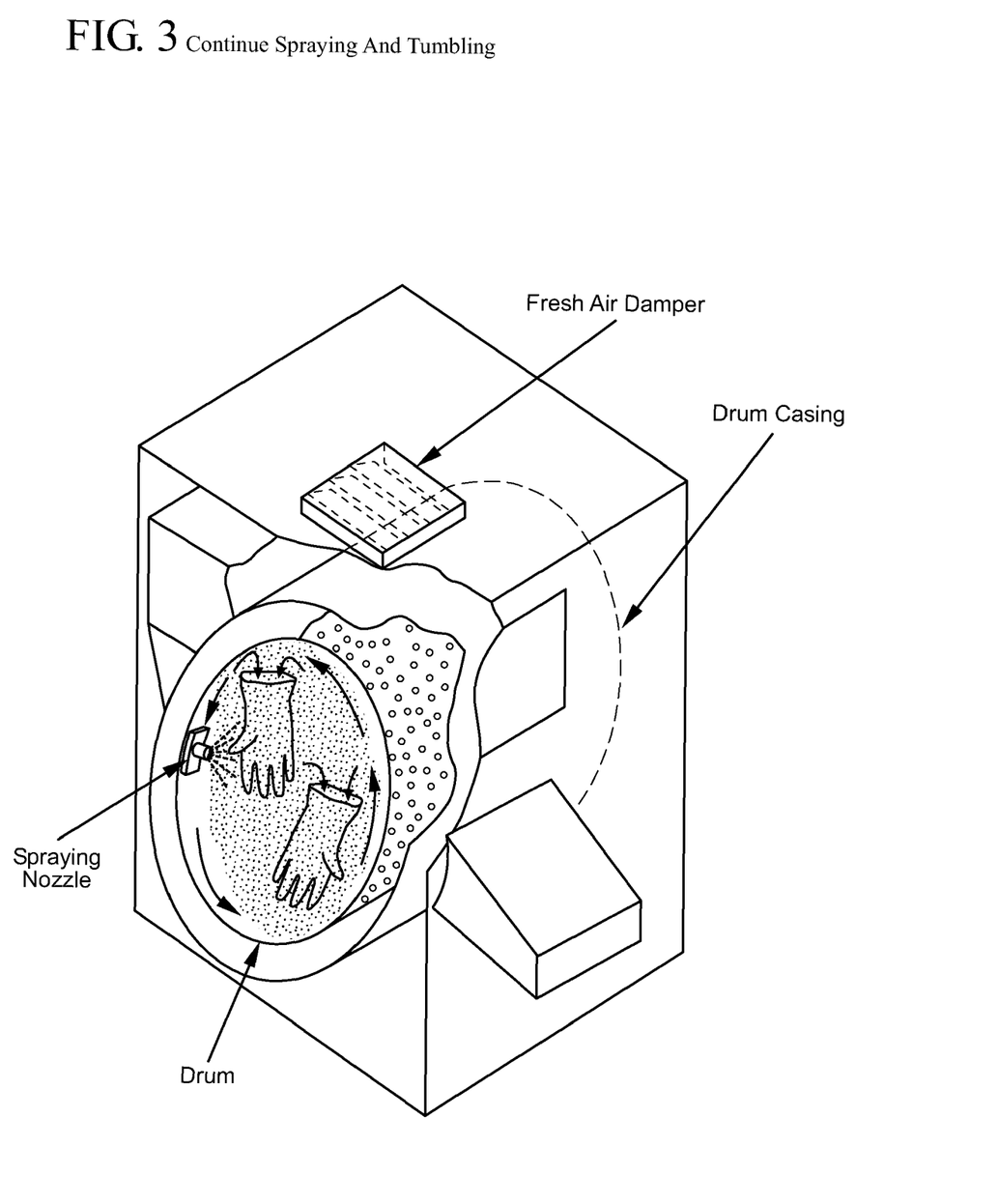
FIG. 3 illustrates the continued spraying of the moisturizing mixture and tumbling of the gloves in the tumble dryer.
Figure 4:
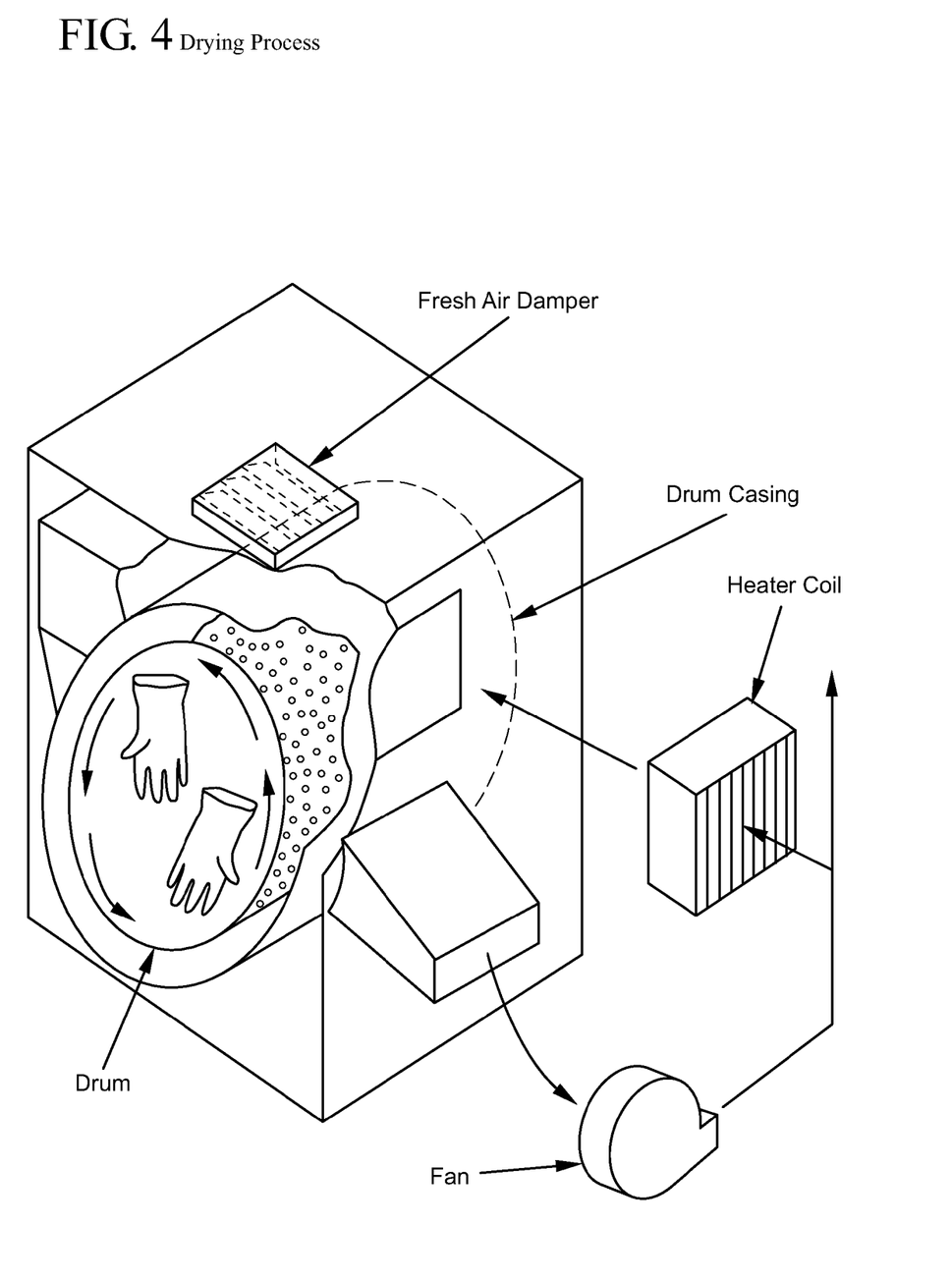
FIG. 4 shows the drying process for the gloves.

The present invention provides a glove which has a film on the interior surfaces of the glove. The film is formed by spraying an untreated glove with a composition containing water, glycerol, and a botanical extract while drying in a tumbler dryer. As the glove is tumbled in a tumbler dyer, the tumbling mechanism allows the composition to creep inside the glove when the glove is partially wet. The water from the surface of the glove acts as a carrier for the composition, enabling the composition to form a film throughout the interior surfaces of the glove. The glove is further dried in the tumbler dryer, however, the resulting interior surfaces are moist to the touch. The embodiments of the instant invention are directed to the treated glove, the composition that is sprayed onto the glove, and the process of forming the film onto the interior surfaces of the glove.

An untreated glove, i.e. a glove that has not been treated with the composition of the present invention, is made from natural rubber latex, polyvinyl chloride, polychloroprene rubber, polyisoprene rubber, butyl rubber, acrylonitrile butadiene rubber (NBR), carboxylated nitrile, polyurethane rubber, polyacrylate, latices of styrene-butadiene rubber and blends of natural rubber latex with synthetic latices.

A preferred untreated glove is a single layer glove manufactured by dipping a heated former into Powder-Free Coagulant (PFC), which is then partially dried in an oven, followed by a single latex dip. A single latex layer is formed on the glove former.

It has been discovered that the composition of the present invention containing the combination of water, glycerol and a botanical extract has hygroscopic properties when applied to the surface of a disposable glove. The hygroscopic nature of the composition is responsible for the treated glove surface retaining moisture when the composition is sprayed on an untreated glove while drying in a tumbler dryer. The amount of moisture retained on the treated surfaces of the glove is between 30 and 90 mg/glove, preferably about 60 mg per glove.

Water is present in the composition of the present invention in an amount ranging from about 75 to about 98 weight percent, preferably from about 85 to about 95 weight percent, based on the total weight of the composition.

Glycerol is a humectant that is commonly used in cosmetics, liquid soaps, and confectioneries for its moisturizing properties. Many botanical extracts are soluble in glycerol; however, glycerol must be present in the composition of the present invention in an amount sufficient to bind the botanical extract onto the interior glove surface and attach to the human skin while wearing the glove. The effective amount of glycerol in the composition ranges from about 1 to about 14 weight percent, preferably from about 1 to about 7 weight percent, based on the total weight of the composition. Relative to a rubber glove weight of 7 to 10 g, the glycerol is present at a range of about 5 to 30 mg inside and 10 to 40 mg outside.

Suitable botanical extracts present in the composition of the present invention may include, but are not limited to, camomile, aloe vera, jojoba, aloe barfadenis extract, passion flower extract, cucumber extract, comfrey leaf extract, saponaria, officinalis extract, myrrh extract, eucalyptus extract, seaweed extracts, and combinations thereof.

A preferred botanical extract is camomile. Another preferred botanical extract is aloe vera. A more preferred embodiment is a combination of camomile and aloe vera. The botanical extract is present in an amount of from about 0.01 to about 2.0 weight percent, preferably from about 0.05 to about 0.5 weight percent, based on the total weight of the composition.

The composition of the present invention may also contain thickeners, anti-blocking polypropylene waxes, wetting agents, fragrances, preservatives, and combinations thereof. The function of a coating thickener is to increase the viscosity of the moisturizer mixture, thereby allowing moisturizers to remain evenly on the glove surface during the tumbling and drying process.

Thickeners include, but are not limited to carboxymethyl cellulose and polysaccharide gum (for example xanthan gum), hydroxyethyl cellulose, polyacrylate, polyvinyl alcohol, and combinations thereof. A preferred thickener is carboxymethyl cellulose. Another preferred thickener is xanthan gum. The thickener is present in an amount from about 0.05 to about 0.6 weight percent, preferably from about 0.1 to about 0.3 weight percent, based on the total weight of the composition.

An anti-blocking wax is present to prevent any blocking phenomenon due to the hygroscopic properties of the composition of the present invention. Anti-blocking waxes include, but are not limited to, paraffin wax, microcrystalline wax, polypropylene wax, and combinations thereof. A preferred anti-blocking wax is polypropylene wax. The anti-blocking polypropylene wax is present in an amount ranging from about 1.0 to about 8.0 weight percent, preferably from about 2 to about 5 weight percent, based on the total weight of the composition.

Wetting agents include, but are not limited to, fatty alcohol ethoxylate, othyl phenol ethoxylate, nonyl phenol ethoxylate, sodium alkyl sulphate, sulphated methyl oleate, and combinations thereof. A preferred wetting agent is fatty alcohol ethoxylate or nonyl phenol ethoxylate. The wetting agent is present in an amount ranging from about 0.1 to about 1.0 weight percent, preferably from about 0.3 to about 0.9 weight percent, based on the total weight of the composition.

Preservatives include, but are not limited to, citric acid, sodium benzoate, potassium sorbate, methyl paraben, sodium sulphite and sodium metabisulphite, and combinations thereof.

Preferred preservatives are citric acid and sodium benzoate. Preservatives are present in an amount ranging from about 0.01 to about 0.5 weight percent, preferably from about 0.05 to about 0.2 weight percent, based on the total weight of the composition.

Fragrances include, but are not limited to, vanilla, lilac, jasmine, rose, lemon floral, strawberry, gardenia, apple spice, banana, pumpkin spice, carnation, honey kiwi, tangerine, mandarin, peppermint, mango, violet, ylang-ylang, cassis, bergamot, grapefruit, rosemary, combinations of the above mentioned fragrances and a complete range of Nivea fragrances.

A preferred fragrance is Nivea scent. Fragrances are present in an amount ranging from about 0.5 to about 10 weight percent, preferably from about 2 to about 8 weight percent, based on the total weight of the composition.

Another embodiment of the invention is directed to a method of applying a film containing the moisturizing composition of the present invention to the interior surfaces of a glove. A cured glove ex-machine is first washed in a tumble washer for a total of two cycles according to the following parameters:

| Off-line Washing | | | | |
|---|---|---|---|---|
| Medium | Volume | Gloves (Qty) | Time per cycle | Temperature |
| Fresh clean water | 1200 liters per tumble washing. Two washing per cycle. | 14,000 pcs per cycle | 34.5 minutes | Ambient |

After washing the cured gloves, the wet gloves are partially dried in an AMBI™/Challenger dryer (available from Texchine Incorporated, USA) or a COSMOS dryer (available from COSMOS Engineering, Malaysia) at a temperature ranging from about 40 to about 70° C., preferably from about 48 to about 55° C. for about 10 to about 50 minutes. While the gloves are partially wet and still drying, an aqueous solution of the moisturizing composition of the present invention is sprayed into the dryer. The amount of moisturizing solution sprayed into the dryer varies from 18 liters to 36 liters per sample of gloves, depending on the moisturizing effect needed for end users. A sample of gloves contains about 14,000 pieces. For optimum moisturizing effect, the preferred amount of moisturizing solution is 36 liters.

A silicone emulsion may also be sprayed into the dryer along with the moisturizing solution. This allows the glove's outer surface to be siliconised. Silicone is used to ensure that the gloves do not block and the glove's outer surface does not become tacky. A preferred silicone emulsion is Silicone LE 45. Silicone emulsion is present in an amount ranging from about 0.5 to about 4.0 weight percent, preferably from about 1.0 to about 2.0 weight percent, based on the total weight of the moisturizing composition.

The gloves are further dried at a temperature of about 48° to about 52° C. for another 3 to 5 hours. The amount of moisturizing composition retained on the surfaces of the glove ranges from about 0.1 to 2.0 mg/glove, preferably from about 0.5 to about 1.5 mg/glove. The size of the gloves ranges from about size 6 to about size 8.

The tumbling mechanism allows the moisturizing composition to coat the glove and creep inside the glove during the initial stage of drying when the gloves are still partially wet. The water on the gloves acts both as a carrier and lubricating medium. Further drying after the spraying of the moisturizing composition causes some, but not all of the water to evaporate, leaving a moist coating formulation on the treated glove surface.

The following examples further illustrate the invention but, of course, should not be construed as in any way limiting its scope.

Comparative Example 1

The moisture content of standard PFC gloves (available from Ansell (Kedah) Sdn Bhd, Kulim Industrial Estate, Kulim, Kedah, Malaysia) was measured according to the following method. Each sample contained ten pieces of size 8 gloves. The ten pieces of gloves were weighed, oven dried at 100° C. for 30 minutes, and weighed after drying. The moisture content was calculated based on the weight of the water lost during drying, calculated by subtracting the weight of the sample after drying from the weight of the sample before drying. The percentage of water lost from drying was calculated as a percentage by the following equation:

$$\frac{\text{Weight of sample before drying} - \text{Weight of sample after drying}}{\text{Weight of sample before drying}} \times 100\%$$

The results are shown in Table 1. All weights are expressed as grams.

TABLE 1

Results for Standard PFC Gloves

| Sample No. | Wt. Before drying | Wt. After drying | Difference in wt. | Percent water lost |
|---|---|---|---|---|
| 1 | 84.0879 | 83.8730 | 0.2149 | 0.2556 |
| 2 | 84.9364 | 84.7228 | 0.2136 | 0.2515 |
| 3 | 84.8714 | 84.5871 | 0.2843 | 0.3350 |
| 4 | 84.5961 | 84.3361 | 0.26 | 0.3073 |

As shown by this comparative example, the weight of the gloves after drying was less than the weight of the gloves before drying, showing that untreated standard PFC gloves contain small amounts of moisture.

Example 2

The moisture content of gloves containing a full strength mixture of the moisturizing composition of the present invention was measured by the following method. A moisturizing composition was prepared by mixing the ingredients listed in Table 2 below.

TABLE 2

Moisturizing Composition

| Material | Batch Quantity |
|---|---|
| Water | 75 to 100 L* |
| *Aloe Vera*/Camomile powder | 0.1 kg |
| Citric Acid | 0.1 kg |
| Sodium Benzoate | 0.1 kg |
| Glycerol/Glycerin | 7.0 kg |
| Fatty Alcohol Ethoxylate/Nonyl Phenol Ethoxilate | 0.875 kg |
| Polypropylene Wax ME 43040 | 5.0 kg |
| Silicone LE45 | 2.0 kg |
| Nivea Scent | 5.5 kg |
| Hydroxyethyl cellulose/Carboxymethyl cellulose/Polysaccharide (Xanthan) gum | 0.3 kg |

*Note: Top up solution with water until volume is 100 liters

Ex-machine cured gloves (14,000 pieces of size 7 gloves) were washed in a tumble washer for a total of two cycles according to the following parameters:

Off-line Washing

| Medium | Volume | Gloves (Qty) | Time per cycle | Temperature |
|---|---|---|---|---|
| Fresh clean water | 1200 liters per tumble washing. Two washing per cycle. | 14,000 pcs per cycle | 34.5 minutes | Ambient |

The washed gloves were then dried in an AMBI™ dryer at a temperature ranging from about 50° to about 55° C. at ambient pressure. A full strength mixture of the above moisturizing composition (a volume of 18 liters) was sprayed into the dryer after one sample of gloves (about 14,000 pieces of size 7 gloves) was dried for about 25 minutes. The gloves were further dried for about 3 hours.

The treated gloves were then weighed, oven dried at 100° C. for 30 minutes, and weighed after drying. As in Comparative Example 1, each sample contained ten gloves. The moisture content was calculated by the same method in Comparative Example 1. The results are shown in Table 3 below. Weights are expressed in grams.

TABLE 3

Results for Gloves Containing Full Strength Composition

| Sample No. | Wt. before drying | Wt. After drying | Difference in Wt. | Percent water loss |
|---|---|---|---|---|
| 1 | 76.0115 | 75.4251 | 0.5864 | 0.7715 |
| 2 | 75.2132 | 74.5835 | 0.6297 | 0.8372 |

Table 2 shows that gloves containing a full strength composition contain significantly greater amounts of moisture (as shown by the percent water loss) than standard PFC gloves (Comparative Example 1).

Example 3

Example 2 was repeated, but with only a 50% moisturizing composition. The volume of mixture was the same (i.e. 18 liters) but the moisturizing composition of Example 2 was diluted 50/50 with water.

The results are illustrated in Table 4. Weights are expressed in grams.

TABLE 4

Results for Gloves Containing 50% Composition

| Sample No. | Wt before drying | Wt. after drying | Difference in wt. | Percent water loss |
|---|---|---|---|---|
| 1 | 76.0052 | 75.6772 | 0.328 | 0.4315 |
| 2 | 74.8594 | 74.5576 | 0.3018 | 0.4032 |

Table 4 shows that, even when only a 50% moisturizing solution is sprayed onto the gloves, the amount of moisture on the treated gloves is twice as much as the standard PFC untreated glove (Comparative Example 1).

Example 4

This example demonstrates the coverage of the composition of the present invention as a film on the interior surface of the glove and the percentage of moisturizers remaining on the glove after the drying process. For measurement purposes, soda ash (sodium carbonate) was introduced into the 36 liters (Trial 1) and 18 liters (Trial 2) of moisturizing solution at a concentration of 200 grams per liter of moisturizing solution. The moisturizing solution with the soda ash was then sprayed into the dryer containing a sample of gloves (14,000 pieces of size 7 gloves) during the drying process.

Two sets of test samples, each consisting of four pieces of wet gloves, were taken from the dryer after 15 minutes of tumbling. Another two sets of test samples, each consisting of four pieces of dried gloves, were taken from the dryer after the drying process was completed. One set of samples was tested on extraction for the whole glove surface and another set was tested on extraction for inner surface only. Each glove was extracted with 100 ml of de-ionized water. Results are expressed as the average value of four pieces of gloves.

The quantity of soda ash on the glove was determined by the following titration. A glove was tied and placed in an extraction bottle containing 100 ml of de-ionized water. The extraction bottle was fixed to an overhead mixer and agitated for about 30 minutes. The extraction was charged into a 250 ml conical flask. Three drops of phenolphthalein were added to the extract. 0.1 M of HCL was added until the pink color disappeared. This is the end point. The results are shown in Table 5.

TABLE 5

| Trial | Volume of moisturizers | Type of glove | Quantity of soda ash remaining on the whole glove per quantity of soda ash applied per glove (%) | | Quantity of soda ash inside the glove per soda ash on whole glove (%) | |
|---|---|---|---|---|---|---|
| | | | Wet Glove (after 15 min tumbling) | Dry Glove (after complete cycle) | Wet Glove (after 15 min tumbling) | Dry Glove (after complete cycle) |
| Trial 1 | 36 L | Camomile/ *Aloe* Exam Glove | 43 | 41 | 56 | 63 |
| Trial 2 | 18 L | Camomile/ *Aloe* Exam Glove | 24 | 29 | 84 | 67 |

The results show that out of the total moisturizer mixture applied into the tumbler dryer, about one third of the moisturizer mixture remained on the gloves after the complete drying process. The coverage of moisturizer mixture inside the glove is about the same as outside surface i.e., 50% on each side. The results also show that the moisturizer mixture was able to reach up to the inner/inside fingertip area.

Example 5

The moisturizing effect was determined using the following hand touch assessment method. A total of eight subjects tested gloves from different sub-lots made with 50% strength moisturizing solution and full strength moisturizing solution. Both hands of a subject were washed, rinsed with cold water, and dried. The hands were further air dried by waving the hands in the air for 30 seconds. The treated gloves were then placed on the hand and warmed for 10 minutes. The subject was then asked to rate the moisturizing effect and scent of the gloves, using the following numbers:
 1=No moisturizing effect/No smell of Nivea scent
 2=perceivable moisturizing effect/good smell of Nivea
 3=good moisturizing effect/excellent smell of Nivea Results are shown in Tables 6 and 7.

TABLE 6

Nivea scented gloves with 50% strength of moisturizing solution

| Sample No. | Moisturizing Effect | Scent level | Test Result |
|---|---|---|---|
| 1 | 2 | 2 | Passed |
| 2 | 2 | 2 | Passed |
| 3 | 2 | 2 | Passed |

TABLE 7

Unscented gloves with full strength of moisturizing solution

| Sample No. | Moisturizing Effect | Scent level | Test Result |
|---|---|---|---|
| 1 | 3 | Not available | Accept |
| 2 | 3 | Not available | Accept |
| 3 | 3 | Not available | Accept |
| 4 | 3 | Not available | Accept |
| 5 | 3 | Not available | Accept |
| 6 | 3 | Not available | Accept |
| 7 | 3 | Not available | Accept |
| 8 | 3 | Not available | Accept |
| 9 | 3 | Not available | Accept |

TABLE 7-continued

Unscented gloves with full strength of moisturizing solution

| Sample No. | Moisturizing Effect | Scent level | Test Result |
|---|---|---|---|
| 10 | 3 | Not available | Accept |
| 11 | 3 | Not available | Accept |

As shown in Tables 6 and 7, the gloves treated with full strength moisturizing solution were rated as having good moisturizing effect. Even gloves treated with only a 50% moisturizing solution were rated as having a perceivable moisturizing effect.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A glove that receives a hand and is moisturizing and non-irritating to skin comprising a cured latex material including an interior surface and a moist surface film comprising
    water in an amount in the range from about 30 mg to about 90 mg,
    glycerol in an amount that is, for a 7 to 10 g glove:
        on the inside in the range from about 5 mg to about 30 mg, and
        on the outside in the range from about 10 mg to about 40 mg, and
    camomile in an amount in the range from about 2 to about 5 wt % based on the total weight of the film,
the moist surface film being disposed on the interior surface and at least a portion of which will attach to the skin while wearing the glove, and wherein the moist surface film is moist to the touch.

2. The glove of claim 1, wherein the moist surface film further comprises a botanical extract selected from the group consisting of *Aloe Vera*, jojoba, aloe barfadenis extract, passion flower extract, cucumber extract, comfrey leaf extract, saponaria, officinalis extract, myrrh extract, eucalyptus extract, seaweed extracts and combinations thereof.

3. The glove of claim 1, wherein the moist surface film further comprises a thickener, an anti-blocking wax, a wetting agent, a fragrance and a preservative.

4. The glove of claim 1 wherein the moist surface film comprises a thickener in an amount in the range from about 0.05 to about 0.6 wt % based on the total weight of the film.

5. The glove of claim 1 wherein the moist surface film comprises an anti-blocking wax in an amount in the range from about 1 to about 8 wt % based on the total weight of the film.

6. The glove of claim 1, wherein the glove comprises an outside surface and a portion of the moist surface film is disposed on the outside surface.

7. A method of forming a glove according to claim 1 comprising:
    providing a plurality of gloves comprising a cured latex layer including an interior surface in an enclosure; and
    spraying a solution comprising water, glycerol and camomile into the enclosure while removing water from the enclosure to form a hygroscopic film comprising water, glycerol and camomile on the interior surface of the cured latex material.

8. The method of claim 7, wherein removing water from the enclosure comprises heating the plurality of gloves.

9. The method of claim 7, wherein the enclosure is a tumble dryer.

10. The method of claim 9, wherein the plurality of gloves are provided partially wet after washing the plurality of gloves with water and drying the water washed glove in the tumbler dryer.

11. The method of claim 10 further comprising spraying an aqueous silicone emulsion on the outer surface of the water washed glove.

12. The method of claim 7, wherein the solution further comprises a botanical extract selected from the group consisting of *Aloe Vera*, jojoba, aloe barfadenis extract, passion flower extract, cucumber extract, comfrey leaf extract, saponaria, officinalis extract, myrrh extract, eucalyptus extract, seaweed extracts and combinations thereof.

13. The method of claim 7, wherein the solution further comprises a thickener, an antiblocking wax, a wetting agent, a fragrance and a preservative.

14. A method of forming a glove according to claim 1 that is moisturizing and non-irritating to skin:
    providing a cured latex glove including an inside portion with an interior surface that is in contact with a hand when worn and an outside surface; and
    utilizing water to carry a solution comprising glycerol and camomile to the interior surface of a glove to form a moist surface film on the interior surface of the cured latex glove to form the treated glove such that the moist surface film will attach to the skin while wearing the glove.

15. The method of claim 14, comprising placing the glove on a hand and at least a portion of the film attaching to the skin to moisturize the hand.

16. The method of claim 14, wherein utilizing the water to carry a solution to the interior surface of a glove comprises;
    washing the glove with water;
    drying the water washed glove of step in a tumbler dryer;
    spraying a solution comprising water, glycerol and camomile into the tumbler dryer onto the outside surface of the water washed glove while it is drying and partially wet; and
    drying the glove until the solution has crept into the inside portion of the glove and a film comprising a portion of the water, the glycerol and the camomile forms on the interior surface.

17. The method of claim 16, wherein the solution further comprises a botanical extract selected from the group consisting of *Aloe Vera*, jojoba, aloe barfadenis extract, passion flower extract, cucumber extract, comfrey leaf extract, saponaria, officinalis extract, myrrh extract, eucalyptus extract, seaweed extracts and combinations thereof.

18. The method of claim 16, wherein the solution further comprises a thickener, an antiblocking wax, a wetting agent, a fragrance and a preservative.

19. A method of forming a glove according to claim 1:
water washing a cured latex glove including an inside portion with an interior surface that is in contact with a hand when worn and an outside surface;
drying the water washed glove of step (a) in a tumbler dryer at a temperature of about 48 to about 55° C.;
spraying a solution comprising water, glycerol and camomile into the tumbler dryer onto the outside surface of the water washed glove while it is drying and partially wet; and
drying the glove such that the solution has crept into the inside portion of the glove and a film comprising a portion of the water, the glycerol and the camomile forms on the interior surfaces of the washed glove.

20. The method of claim 19, wherein the solution further comprises a botanical extract selected from the group consisting of *Aloe Vera*, jojoba, aloe arfadenis extract, passion flower extract, cucumber extract, comfrey leaf extract, saponaria, officinalis extract, myrrh extract, eucalyptus extract, seaweed extracts and combinations thereof.

21. The method of claim 19, wherein the solution further comprises a thickener, an antiblocking wax, a wetting agent, a fragrance and a preservative.

22. A method of moisturizing a human hand comprising:
providing a glove according to claim 1; and
inserting a dry hand into the glove such that the hand contacts the moist surface film causing the glycerol and camomile of the moist surface film to attach to skin, thereby moisturizing the hand.

23. The method of claim 22, wherein the moist surface film further comprises a botanical extract selected from the group consisting of *Aloe Vera*, jojoba, aloe barfadenis extract, passion flower extract, cucumber extract, comfrey leaf extract, saponaria, officinalis extract, myrrh extract, eucalyptus extract, seaweed extracts and combinations thereof.

24. The method of claim 22, wherein the moist surface film further comprises a thickener, an anti-blocking wax, a wetting agent, a fragrance and a preservative.

25. The glove of claim 1, wherein the surface film is essentially free of alcohol.

26. The glove of claim 1, wherein the for smaller or larger gloves, glycerol is in amounts calculated relative to the above ranges for the inside and outside.

\* \* \* \* \*